United States Patent
Putz

(10) Patent No.: US 7,465,292 B2
(45) Date of Patent: Dec. 16, 2008

(54) CATHETER SYSTEM FOR INTRACRANIAL TREATMENT

(75) Inventor: David A. Putz, Pewaukee, WI (US)

(73) Assignee: Ad-Tech Medical Instrument Corp., Racine, WI (US)

( * ) Notice: Subject to any disclaimer, the term of this patent is extended or adjusted under 35 U.S.C. 154(b) by 35 days.

(21) Appl. No.: 11/262,376

(22) Filed: Oct. 28, 2005

(65) Prior Publication Data

US 2006/0079857 A1    Apr. 13, 2006

Related U.S. Application Data

(63) Continuation-in-part of application No. 10/423,587, filed on Apr. 25, 2003, now Pat. No. 7,241,283.

(51) Int. Cl.
*A61M 5/178* (2006.01)

(52) U.S. Cl. .................. 604/164.09; 604/158

(58) Field of Classification Search .......... 604/171, 604/173, 272, 93.01, 158, 164.01–164.11, 604/170.01–170.02, 167.01, 167.02, 167.06
See application file for complete search history.

(56) References Cited

U.S. PATENT DOCUMENTS

| | | | |
|---|---|---|---|
| 4,346,709 A | 8/1982 | Schmitt | |
| 4,471,779 A | 9/1984 | Antoshkiw et al. | |
| 4,613,324 A | 9/1986 | Ghajar | |
| 4,685,901 A | 8/1987 | Parks | |
| 4,777,951 A | 10/1988 | Cribier et al. | |
| 4,798,586 A | 1/1989 | Stevens | |
| 4,892,538 A | 1/1990 | Aebischer et al. | |
| 4,921,478 A | 5/1990 | Solano et al. | |
| 5,033,998 A | 7/1991 | Corday et al. | |
| 5,041,090 A | 8/1991 | Scheglov et al. | |
| 5,064,654 A | 11/1991 | Berner et al. | |
| 5,081,990 A | 1/1992 | Deletis | |
| 5,087,244 A | 2/1992 | Wolinsky et al. | |
| 5,106,376 A * | 4/1992 | Mononen et al. ....... | 604/164.11 |
| 5,119,832 A | 6/1992 | Xavier | |
| 5,147,315 A * | 9/1992 | Weber .................... | 604/164.09 |
| 5,147,335 A * | 9/1992 | Wright ........................ | 604/540 |
| 5,154,179 A | 10/1992 | Ratner | |
| 5,191,898 A | 3/1993 | Millar | |
| 5,330,768 A | 7/1994 | Park et al. | |
| 5,423,877 A | 6/1995 | Mackey | |
| 5,458,631 A | 10/1995 | Xavier | |

(Continued)

*Primary Examiner*—Nicholas D Lucchesi
*Assistant Examiner*—Theodore J Stigell
(74) *Attorney, Agent, or Firm*—Jansson Shupe & Munger Ltd.

(57) ABSTRACT

A catheter system is provided having an outer catheter and at least one inner catheter chosen from a plurality of different inner catheters for delivery of a treatment agent to a selected tissue region of the brain. The outer catheter has a lumen in communication with an opening and at least one aperture. Each inner catheter is sized to be received within the lumen and has a passageway and at least one port in communication with that passageway. The system preferably has inner catheters having different lengths and/or passageways with different diameters. The outer catheter can include an element that monitors brain activity. The outer catheter can also have an inflatable balloon proximal to an element. A method of delivering a treatment agent, preferably a drug, to a select tissue region of a targeted area of the brain for intracranial treatment of a patient is also disclosed.

27 Claims, 7 Drawing Sheets

U.S. PATENT DOCUMENTS

| | | |
|---|---|---|
| 5,505,698 A | 4/1996 | Booth et al. |
| 5,662,607 A | 9/1997 | Booth et al. |
| 5,676,655 A | 10/1997 | Howard et al. |
| 5,697,975 A | 12/1997 | Howard et al. |
| 5,711,316 A | 1/1998 | Elsberry et al. |
| 5,713,858 A | 2/1998 | Heruth et al. |
| 5,728,066 A | 3/1998 | Daneshvar |
| 5,782,798 A | 7/1998 | Rise |
| 5,792,100 A | 8/1998 | Shantha |
| 5,792,110 A | 8/1998 | Cunningham |
| 5,795,331 A | 8/1998 | Cragg et al. |
| 5,807,328 A | 9/1998 | Briscoe |
| 5,810,767 A | 9/1998 | Klein |
| 5,843,022 A | 12/1998 | Willard et al. |
| 5,868,704 A | 2/1999 | Campbell et al. |
| 5,975,085 A * | 11/1999 | Rise .................... 128/898 |
| 6,017,323 A | 1/2000 | Chee |
| 6,041,252 A | 3/2000 | Walker et al. |
| 6,096,021 A | 8/2000 | Helm et al. |
| 6,120,477 A | 9/2000 | Campbell et al. |
| 6,203,526 B1 * | 3/2001 | McBeth et al. .......... 604/96.01 |
| 6,210,346 B1 | 4/2001 | Hall et al. |
| 6,241,734 B1 * | 6/2001 | Scribner et al. ............... 606/93 |
| 6,251,115 B1 | 6/2001 | Williams et al. |
| 6,263,225 B1 | 7/2001 | Howard, III |
| 6,264,633 B1 | 7/2001 | Knorig |
| 6,272,370 B1 * | 8/2001 | Gillies et al. ................ 600/411 |
| 6,283,951 B1 * | 9/2001 | Flaherty et al. ............. 604/529 |
| 6,510,347 B2 | 1/2003 | Borkan |
| 6,527,782 B2 | 3/2003 | Hogg et al. |
| 6,544,206 B1 * | 4/2003 | Johnston, Jr. .............. 604/4.01 |
| 6,629,990 B2 | 10/2003 | Putz et al. |
| 6,656,152 B2 | 12/2003 | Putz |
| 6,730,061 B1 * | 5/2004 | Cuschieri et al. ............ 604/158 |
| 6,733,474 B2 | 5/2004 | Kusleika |
| 6,773,447 B2 | 8/2004 | Laguna |
| 6,832,115 B2 | 12/2004 | Borkan |
| 6,887,229 B1 | 5/2005 | Kurth |

* cited by examiner

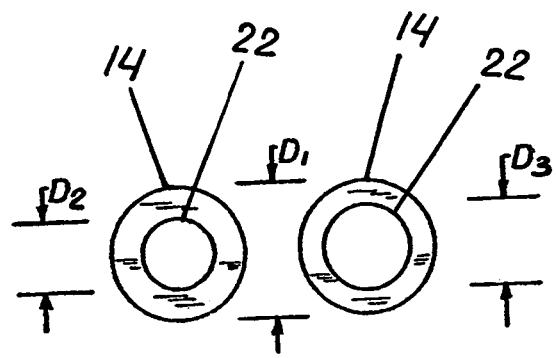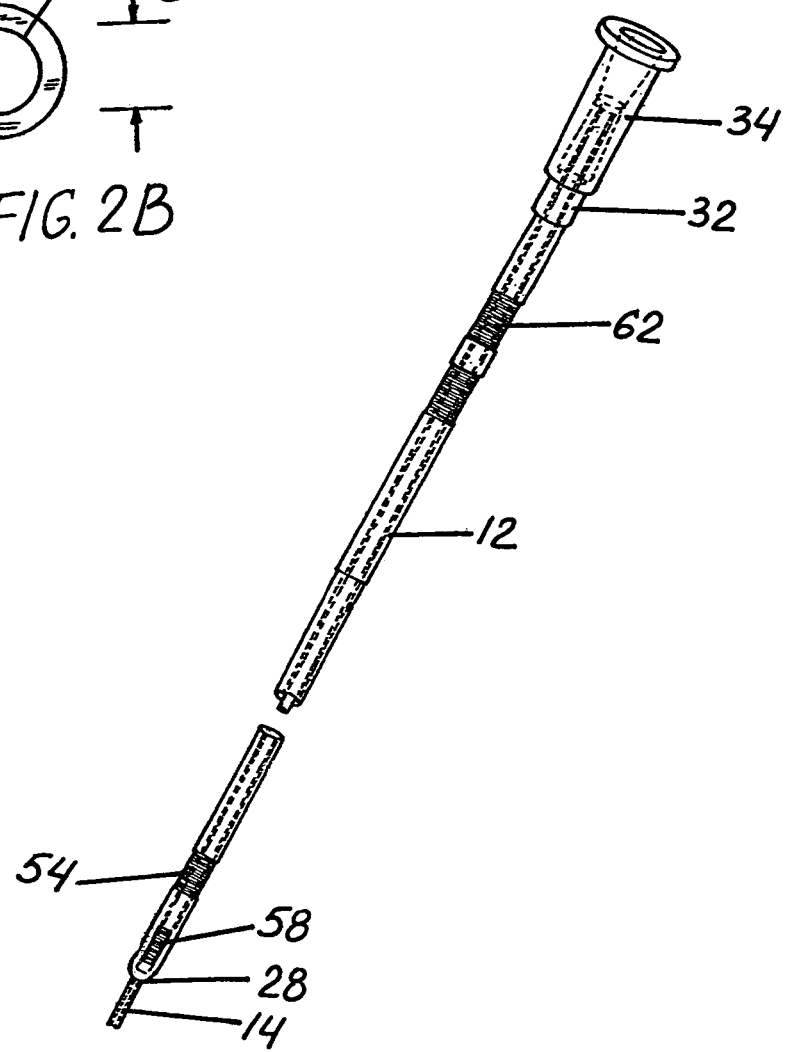

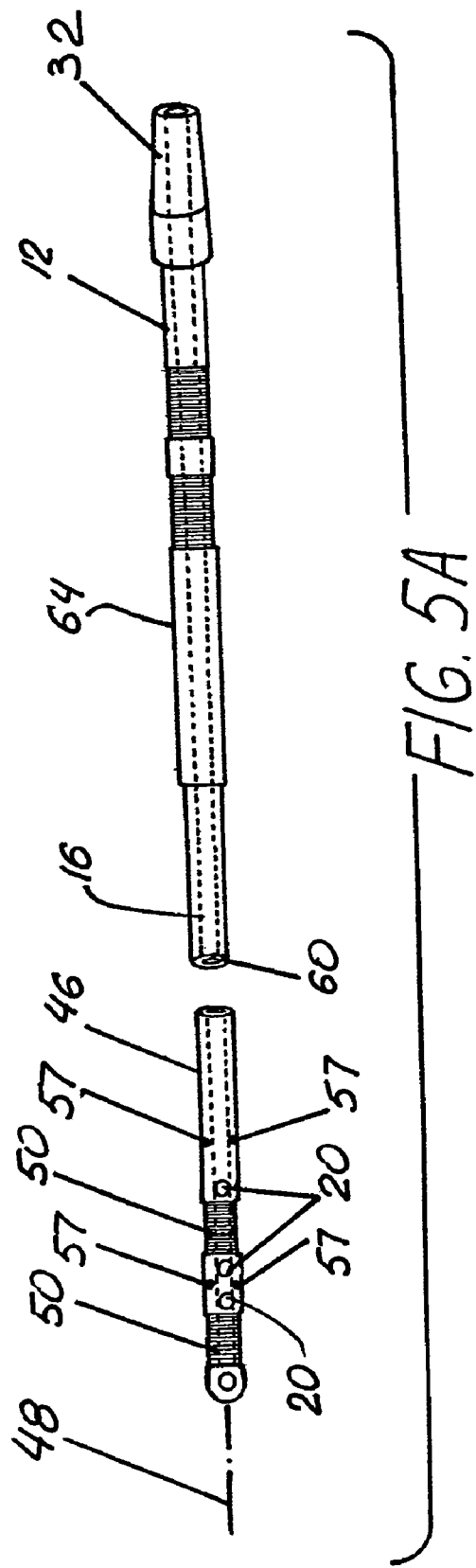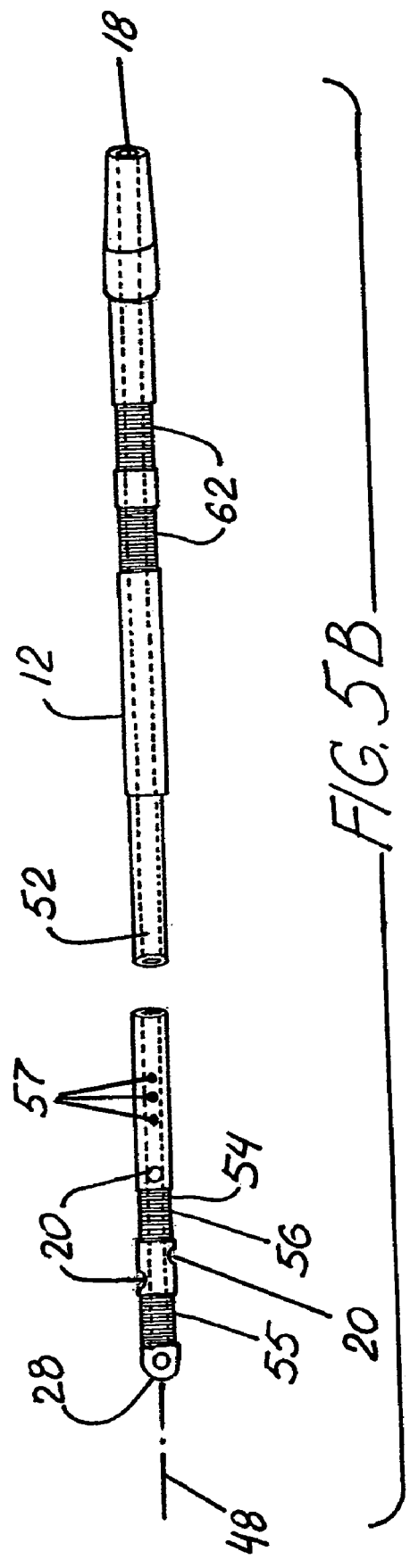

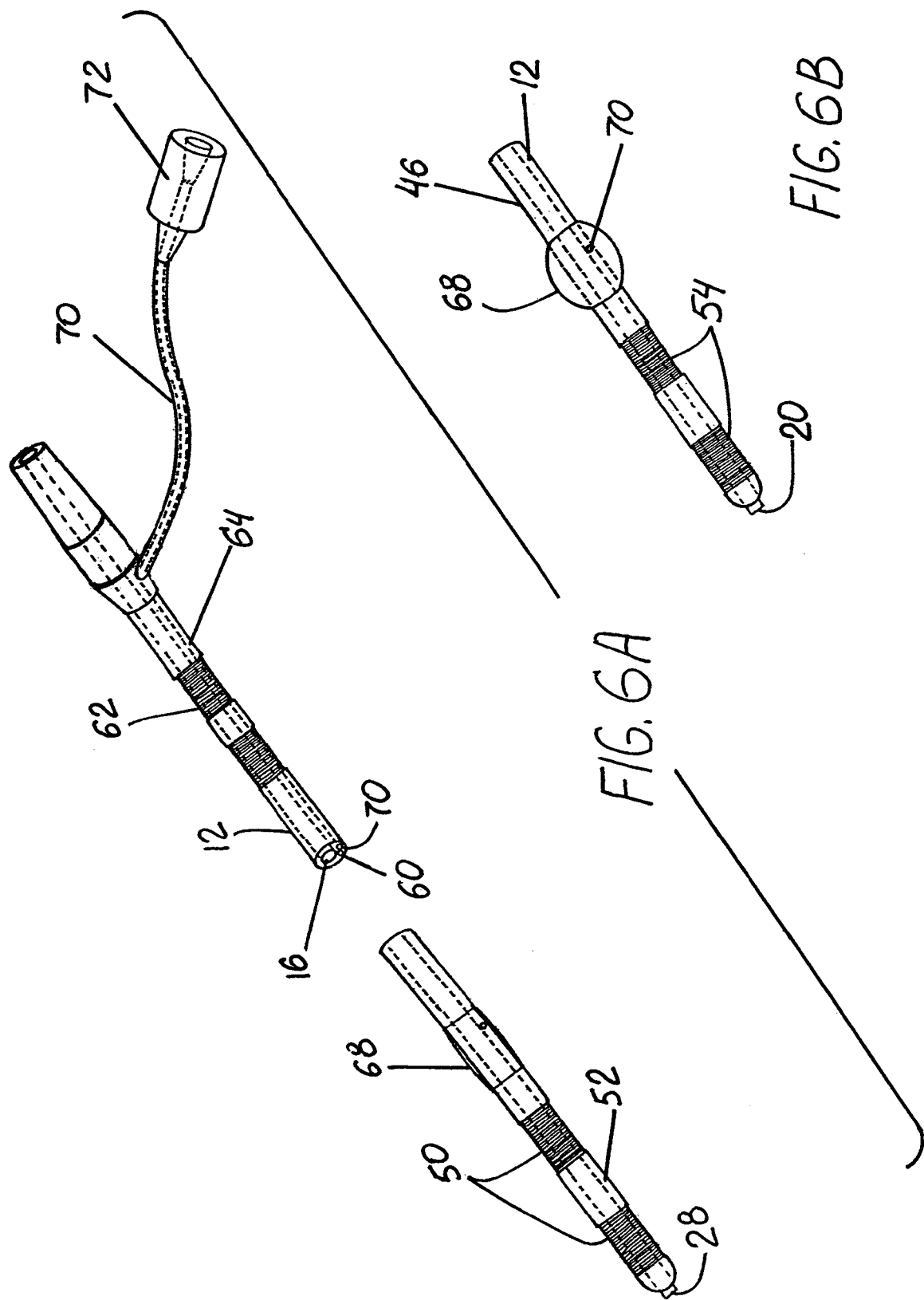

CATHETER SYSTEM FOR INTRACRANIAL TREATMENT

RELATED APPLICATION

This application is a continuation-in-part of U.S. patent application Ser. No. 10/423,587, filed on Apr. 25, 2003 now U.S. Pat. No. 7,241,283.

FIELD OF INVENTION

The present invention relates to catheter systems for intracranial treatment and, in particular, to catheter systems for the intracranial delivery of a treatment agent.

BACKGROUND OF THE INVENTION

Movement disorders such as epilepsy and Parkinson's disease have been estimated to affect some 1-2% of the developed world's population and up to 10% of people in underdeveloped countries. Currently, approximately 75% of those who suffer from movement disorders are responsive in some degree to drugs.

Electrical stimulation has also been utilized to treat some movement disorders. In the treatment of epilepsy, studies have been performed in which awake patients undergoing temporal lobe surgery underwent cortical stimulation. Such stimulation of the visual and hearing areas of the brain reproducibly caused the patients to experience visual and auditory phenomena. This discovery was made possible by the identification that certain brain subregions served specific functions, such as sight, hearing, touch and movement of the extremities and proved that direct electrical stimulation of the brain regions could cause partial reproduction or suppression of the functions.

As suggested by these results, it is known that certain types of treatment of specific portions of the brain are able to suppress certain unwanted behavior which results from movement disorders. This behavior may include seizures such as those suffered by epileptics. However, the studies faced a major problem in that there was an inability to precisely electrically stimulate very small volumes of the brain.

The advent of needle-shaped penetrating depth electrodes helped to overcome this obstacle faced by electrical stimulation. Depth electrodes can be placed within the brain tissue itself, enabling optimal surface contact with elements of the brain that are targeted for stimulation. This allowed for safe, chronic electrical stimulation of very small discrete volumes of brain.

In treatment, electrical stimulation has been used with the recording and analysis of changes in brain activity to predict the occurrence of epileptic seizures. The time of onset of such seizures is often predictable by neural discharge monitoring, even when the exact causal nature of precipitating dysfunction is not understood. Electrodes have been used to obtain signals representative of current brain activity along with a signal processor for continuous monitoring and analysis of these electrical signals in order to identify important changes or the appearance of precursors predictive of an impending change.

While the electrical stimulation of brain tissue has been somewhat effective in the treatment of migraines, epilepsy and other neurological problems, patients often experience diminishing returns with such treatment. Furthermore, because each patient reacts differently to electrical stimulation, substantial time must be spent to determine the specific amplitude, frequency, pulse width, stimulation duration, etc. which may result in effective treatment. In addition, such parameters often require continual adjustment in order to remain effective.

Improved intracranial monitoring devices have been shown to facilitate treatments of movement disorders. Monitoring is typically performed by instruments which are inserted into the brain at different locations or along different tracks. Other systems employ a single device which must be removed and reinserted to provide for delivery of multiple drugs or use of different electrical devices.

Since the introduction of probes or other similar devices into the brain is common in many surgical procedures today, there are a variety of probes available. Such probes typically include ports for drug delivery or electrical, chemical, electrochemical, temperature and/or pressure contacts which enable the observation and analysis of the brain state or contacts providing stimulation. These ports and contacts must typically be positioned at specific points or regions in the brain.

Probes used in intracranial penetration are typically fabricated so that their introduction to the brain is as minimally traumatic as possible. In addition to being minimally traumatic during insertion, certain inserted probes must also be able to remain implanted without causing injury through unintended movement. In some uses, a probe may be implanted and remain in the patient's brain for weeks or longer. Changes in the positioning of the probe often occur during placement or during such extended periods. Therefore, the probe must be capable of precise placement and as bio-compatible as possible. In response to these requirements, state of the art intracranial probes are typically thin, flexible pieces with smooth surfaces to minimize the amount of brain tissue contacted and to minimize damage to contacted brain tissue.

While such thin, flexible probes are sufficiently bio-compatible, they are delicate and often difficult to insert along specific trajectories or lines of insertion. During typical implantation, a surgeon feeds the probe into the brain through an aperture in the skull. In this process, the surgeon has very little control over the distal end of the probe. In order to provide more rigidity to the probe to overcome this problem, a removable stylet may be inserted into the probe before implantation. Still, veering from the intended line of insertion is not altogether prevented by introduction of a stylet to the probe.

There is a continuing significant need in the field of intracranial treatment, particularly with insertion of probes into the interior of the brain, for improvements in accuracy of insertion and avoidance of injury, while retaining efficiency and ease of use.

In addition, there is a need in the field of intracranial treatment to minimize the invasiveness of intracranial treatment and to reduce the number of instruments which penetrate brain tissue or the number of times a single instrument must penetrate brain tissue.

Furthermore, there is a need in the field of intracranial treatment to provide the ability to precisely locate the position of a probe during insertion to ensure proper positioning.

OBJECTS OF THE INVENTION

It is a primary object of the invention to provide an improved intracranial catheter system that overcomes some of the problems and shortcomings of the prior art.

Another object of the invention is to provide a novel catheter system which is simple in structure and operation in order to facilitate intracranial procedures.

Another object of the invention is to provide an exceptional catheter system having a plurality of different inner catheters that allows for the precise delivery of a treatment agent to a select tissue region of the brain while avoiding extensive trauma to and scarring of brain tissue.

Another object of the invention is to provide an excellent catheter system having an outer catheter which includes contacts for stimulation and/or for monitoring the brain and which receives and guides an inner catheter for delivering a treatment agent to targeted brain tissue.

Another object of the invention is to provide a desirable catheter system having an outer catheter which receives and guides one of a plurality of inner catheters having different lengths and/or different inner diameters for delivering drugs to targeted brain tissue and remains in position when each inner catheter is removed, allowing for repeated insertions of the different inner catheters without extended contact with brain tissue during insertion.

Another object of the invention is to provide a novel catheter system having an outer catheter that includes a permeable balloon capable of being inflated with a drug for introduction of the drug into the brain at a controlled rate.

Yet another object of the invention is to provide an improved method for intracranial treatment wherein an outer catheter inserted into a targeted area of the brain is used to reliably guide to a specific tissue region an inner catheter chosen from a plurality of different inner catheters for the delivery of a treatment agent.

SUMMARY OF THE INVENTION

The invention is for a catheter system to provide intracranial treatment of a patient. The catheter system comprises an outer catheter and at least one inner catheter chosen for delivery of a treatment agent to a specifically selected tissue region of the brain from a plurality of different inner catheters. The outer catheter has a lumen in communication with an opening and at least one aperture. Each inner catheter is sized to be received within the lumen and has a passageway and at least one port in communication with that passageway.

In certain preferred embodiments, first and second inner catheters are chosen from the plurality of inner catheters where the first inner catheter has a first length for delivering the treatment agent to a first tissue region and the second inner catheter has a second length for delivering the treatment agent to a second tissue region. A more desirable embodiment finds each inner catheter is adapted to extend through the aperture when it is inserted into the lumen, preferably where the aperture is positioned at the outer catheter's distal end. In these embodiments, it is highly desirable for the second length to be greater than the first length so that the second tissue region is at a greater distance distal from the aperture than the first tissue region.

Much preferred is where the port on each inner catheter is positioned at its distal end. Highly preferred is where each inner catheter has a plurality of ports in different arrangements.

In other embodiments that are found desirable, the treatment agent is a fluid, preferably a drug. Certain highly desirable cases find the passageway of the first inner catheter to have a first diameter and the passageway of the second inner catheter to have a second diameter. The second diameter is greater than the first diameter to permit the delivery of the fluid to the second tissue region at a different flow rate than the delivery of the fluid to the first tissue region.

Another preferred embodiment finds the outer catheter having first and second apertures spaced axially along its exterior. Much preferred is where the first and second apertures are also spaced radially about the axis of the catheter.

One very desirable embodiment has the outer catheter including an element. More desirable is where the element is a contact that monitors brain activity, preferably electrical activity. Also desirable is where the contact is a micro-contact. In certain cases, the element is a contact that stimulates brain activity. Other preferred examples have the element being a location marker to identify the position of the outer catheter within the brain. A highly desirable number of embodiments find the element to be a sensor, preferably one that can sense the brain's chemical activity.

Another embodiment found preferred is where the outer catheter includes a conduit extending from its proximal portion to an inflatable balloon secured to its exterior. More preferred is where the balloon is inflatable with at least one drug, the balloon being formed from a material permeable to the drug so that the drug can be introduced into the brain through the balloon. Very desirable is where the balloon is positioned just above the aperture and is adapted to seal, when inflated, the tract created when the outer catheter is inserted into the brain. Highly preferred is where the balloon is positioned along the outer catheter proximal to at least one element.

Certain desirable examples of this invention find the opening of the outer catheter located at its proximal end. With such embodiments, more desirable is where the outer catheter also has a tapered fitting at the proximal end that is configured for removable engagement to a fitting at the proximal end of each inner catheter. Much preferred is where the proximal end of the outer catheter abuts a threaded exterior portion such that the outer catheter can be screwed into the skull of the patient after the outer catheter is inserted into a targeted area within the patient's brain. Highly desirable is where, with these embodiments, the inner catheter is then threadably receivable by the outer catheter to firmly secure the one to the other.

Another aspect of this invention finds a method for intracranial treatment having the steps of (1) inserting an outer catheter into a targeted area of the brain of a patient where the outer catheter has a lumen in communication with an opening and at least one aperture; (2) inserting an inner catheter into the outer catheter at the opening where the inner catheter is chosen from a plurality of different inner catheters so that a treatment agent can be delivered to a select tissue region of the targeted area, each of the inner catheters having a passageway in communication with at least one port; (3) utilizing the outer catheter to guide the inner catheter to the tissue region; and (4) delivering the treatment agent to the tissue region through the port.

In certain desirable embodiments, the inner catheter is a first inner catheter having a first length and the outer catheter is utilized to guide this first inner catheter so that the treatment agent is delivered to a first tissue region of the targeted area through the first inner catheter's port. These embodiments of the method also include the steps of inserting into the outer catheter at the opening a second inner catheter having a second length where the catheter is also chosen from the plurality of inner catheters and of using the outer catheter to guide this second inner catheter to deliver the treatment agent to a second tissue region of the targeted area through its port.

With such embodiments, it is preferred that the steps of inserting the first and second inner catheters into the outer catheter include extending the inner catheter through the aperture into the targeted area. More preferred is where the aperture is positioned at the distal end of the outer catheter. Highly preferred is where the second length is greater than the first length to allow the second inner catheter to be extended a greater distance away from the aperture than the first inner catheter.

One desirable embodiment finds each inner catheter having its port positioned at the distal end of the catheter. Very desirable is where each inner catheter has a plurality of ports in a distinct arrangement.

Certain examples of this method find the treatment agent to be a fluid, preferably a drug. A desirable method with such embodiments is to include the step of delivering the fluid to the passageway of each inner catheter at a select pressure, the passageway of the first inner catheter having a first diameter and the passageway of the second inner catheter having a second diameter greater than the first diameter. In this manner, the delivery of the fluid to the second tissue region is at a different flow rate than the delivery of the fluid to the first tissue region.

Much preferred is where the outer catheter has at least first and second apertures, these apertures being spaced axially and radially about the axis of the catheter along its exterior. A highly preferred embodiment of the method is where the intracranial treatment is one directed against tumors.

Another desirable embodiment is where the opening is positioned at the proximal end of the outer catheter and each inner catheter has a tapered fitting at its proximal end, the tapered fitting being configured so that the inner catheter can be removably engaged to the outer catheter at its proximal end. More desirable is where the outer catheter includes a threaded exterior portion at its proximal end and the step of inserting the outer catheter includes screwing the threaded portion into the skull of the patient so that the outer catheter can be retained in the targeted area for an extended period of time. Highly desirable is where the step of inserting the inner catheter into the outer catheter includes baying the inner catheter threadably received by (i.e., screwed into) the outer catheter to firmly secure the inner catheter to the outer catheter. In other embodiments, the outer catheter includes a distal portion having a distal end and at least one sensor mounted proximal to the distal end upon an exterior surface of the distal portion A number of preferred cases of this method find the outer catheter having a location marker and including the step of identifying the position of the location marker within the brain. Also very desirable is where the outer catheter includes a contact mounted on the exterior surface of its distal portion above its distal end and where the method includes the step of monitoring brain activity with the contact during treatment, preferably where the brain activity is electrical activity. Most desirable is where the outer catheter includes a sensor mounted on the exterior surface of the distal portion above the distal end, the method adding the step of sensing brain activity with the sensor during treatment. Highly preferred is where the brain activity being sensed is chemical activity.

Also desirable is where the outer catheter is found to include an inflatable balloon that is secured to its exterior with a conduit extending from it to a proximal portion of the outer catheter. This embodiment also includes the steps of inflating the balloon with at least one drug and introducing the drug(s) into the brain through the balloon since the balloon is formed from a material permeable to the drug(s). Most desirable is where the balloon is positioned just above the aperture and the method includes the step of inflating the balloon to seal a tract created during the insertion of the outer catheter into the brain.

BRIEF DESCRIPTION OF THE DRAWINGS

FIG. 2A is a cross-section view taken substantially along the line 2A-2A of FIG. 1.

FIG. 2B is a cross-section view taken substantially along the line 2B-2B of FIG. 1.

FIG. 3 is a perspective view of another preferred outer catheter in accordance with this invention having received an inner catheter with cut-away sections to reveal and dashed lines to represent otherwise unseen internal features.

FIGS. 5A and 5B are perspective views of alternate preferred outer catheters in accordance with this invention with cut-away sections to reveal and dashed lines to represent otherwise unseen internal features.

FIG. 6A is a perspective view of a preferred outer catheter having a balloon shown deflated in accordance with this invention with cut-away sections to reveal and dashed lines to represent otherwise unseen internal features.

FIG. 6B is the distal end of the outer catheter of FIG. 6A showing the balloon inflated with cut-away sections to reveal and dashed lines to represent otherwise unseen internal features.

DETAILED DESCRIPTION OF PREFERRED EMBODIMENTS

Figure 1:
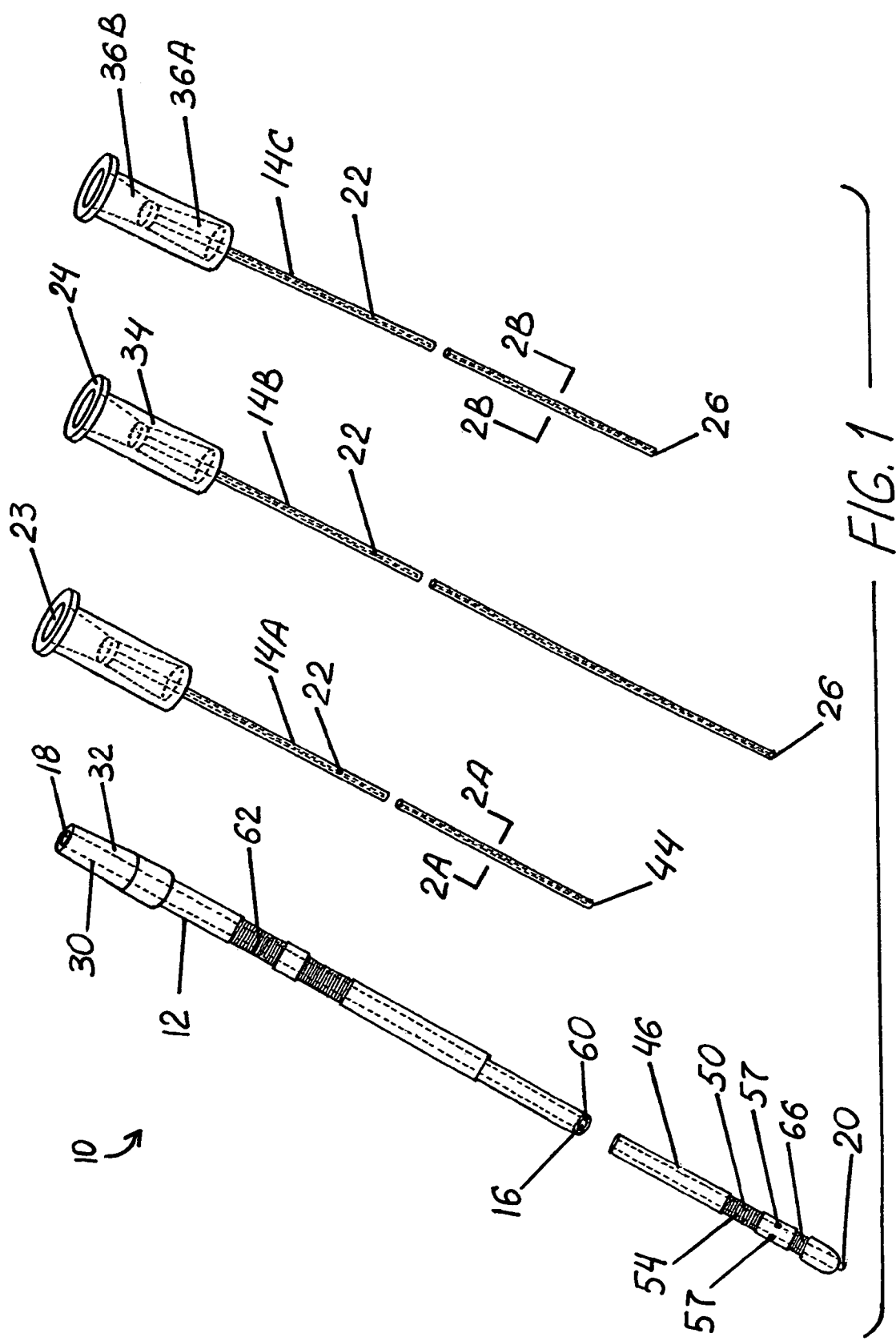
FIG. 1 is a perspective view of a preferred catheter system in accordance with this invention with cut-away sections to reveal and dashed lines to represent otherwise unseen internal features.

The figures illustrate preferred embodiments of an improved catheter system for intracranial treatment of a patient in accordance with this invention. FIG. 1 is a perspective view of catheter system 10 comprising of an outer catheter 12 and a plurality of inner catheters 14A-14C. Outer catheter 12 and each inner catheter 14 cooperate to deliver a treatment agent, preferably a drug in the form of a fluid, to a select tissue region in a targeted area of a patient's brain.

Outer catheter 12 is an elongated, tubular structure having a diameter preferably between about 0.6 and 3.0 millimeters, most preferably about 1.0 millimeter. As illustrated in FIG. 1, outer catheter 12 is provided with lumen 16 extending from opening 18 and in communication with aperture 20. Lumen 16 is a tubular channel extending for some length within outer catheter 12 and sized to receive inner catheter 14, i.e., having a diameter slightly greater than the outside diameter of inner catheter 14. Lumen 16 preferably has a diameter of 0.5 millimeters or less.

Outer catheter 12 is preferably substantially flexible, formed from bio-compatible materials such as polyurethane, silicone, or polyimide. In certain embodiments, outer catheter 12 can also be in the form of a cannula made from a substantially rigid material that is preferably MRI safe/compatible. Such preferable materials are platinum, titanium, polyimide-coated glass, and other non-ferrous alloys. During surgery, when in the form of a cannula, outer catheter 12 could be used with a stereotatic frame or a frameless guidance system to accurately position the catheter within the brain.

A stylet (not shown) is often used during insertion of outer catheter 12 into the brain. The stylet has a diameter or thickness slightly smaller than the diameter of lumen 16 so that it can be inserted within outer catheter 12. The stylet is rigid to allow for precise positioning of outer catheter 12 inside the brain, preferably formed from stainless steel, tungsten or other non-ferrous MRI safe/compatible alloys. In addition to giving added rigidity to outer catheter 12 when placing it within the brain, the stylet prevents brain tissue from entering lumen 16 and thereby outer catheter 12 through aperture 20 during the insertion process.

Inner catheter 14 is preferably polyimide, polyimide-coated glass or other similar material. Inner catheter 14 is provided with passageway 22 which extends from mouth 23 at proximal end 24 to port 26. Port 26, as shown on inner catheters 14A-14C in FIG. 1, is coaxial with passageway 22. Applicant notes that one such preferred catheter is disclosed in U.S. patent application Ser. No. 10/423,587 filed by Applicant on Apr. 25, 2003, the disclosure of which is incorporated by reference herein.

The set of three inner catheters 14A-14C depicted in FIG. 1 are each different. Inner catheter 14B has a different length than inner catheters 14A, 14C. As illustrated in FIGS. 2A and 2B, inner catheters 14A and 14C have an identical outer diameter $D_1$. Inner catheter 14A has, however, an inner diameter $D_2$ for passageway 22 that is less than inner diameter $D_3$ of inner catheter 14C.

Inner catheters 14A-14C are preferably used with an outer catheter 12 having an open distal end 28 such that at least one aperture 20 is coaxial with lumen 16. In this embodiment, after inserting outer catheter 12 into the patient's brain, a first inner catheter 14A of a specific length and inner diameter is selected to treat a desired tissue region at a known location beyond outer catheter 12 by extending the inner catheter through aperture 20 as shown in FIG. 3. After treatment at that location, first inner catheter 14A can be removed and a second inner catheter 14B having a longer length can be inserted into the patient's brain to treat a different desired tissue region. For instance, an inner catheter 14 which extends 0.5 cm beyond outer catheter 12 may be used to treat the tissue region 0.5 cm beyond outer catheter 12 and then removed from first lumen 16 before another inner catheter 14 which extends 2.0 cm beyond distal end 30 of outer catheter 12 is inserted through first lumen 16 and used to treat the tissue region 2.0 cm beyond outer catheter 12.

In the alternative, after first inner catheter 14A had been removed from outer catheter 12, a third inner catheter 14C having a wider inner diameter could be inserted to treat the same or a different selected tissue region. By varying the inner diameter of the inner catheter selected, the desired flow rate of a fluid treatment agent through that inner catheter can be varied at a selected pressure. The inner diameter of inner catheter 14 will preferably range from 25 microns to 0.5 millimeters.

It will be readily recognized that the set of inner catheters 14 provided as a catheter system with outer catheter 12 can be any number. This choice of inner catheters 14 is so that a physician can select a specific inner catheter 14 to treat one of a number of desired tissue regions without requiring multiple insertions of a catheter capable of delivering a treatment agent through the intervening brain tissue. This is particularly useful when treating different tissue regions in and around tumors with different drugs or different concentrations of the same drug.

The proximal end 30 of outer catheter 12 is provided with a tapered fitting 32, preferably a male luer conical fitting. Opening 18 is preferably located at proximal end 30 and coaxial with lumen 16. Proximal end 24 of inner catheter 14 is provided with a tapered coupler 34, preferably a luer coupler that has female luer fittings 36A, 36B at both of its ends. Tapered coupler 34, as illustrated in FIG. 3, enables inner catheter 14 to form a detachable air-tight joint with outer catheter 12 when inner catheter 14 is fully inserted into lumen 16 through opening 18. Tapered fitting 32 of outer catheter 12 is snugly received by fitting 36A at the distal end of tapered coupler 34 on inner catheter 14. Fitting 36B on the proximal end of tapered coupler 34 enables inner catheter 14 to be operatively connected by tubing to an external piece of equipment such as a pump. One skilled in the art will recognize that inner catheter 14 could also be connected to internal instrumentation having pumping capability. This process enables treatments agents such as drugs to be administered to a specific tissue region of the brain 38 through port 26.

Figures 4A, 4B:
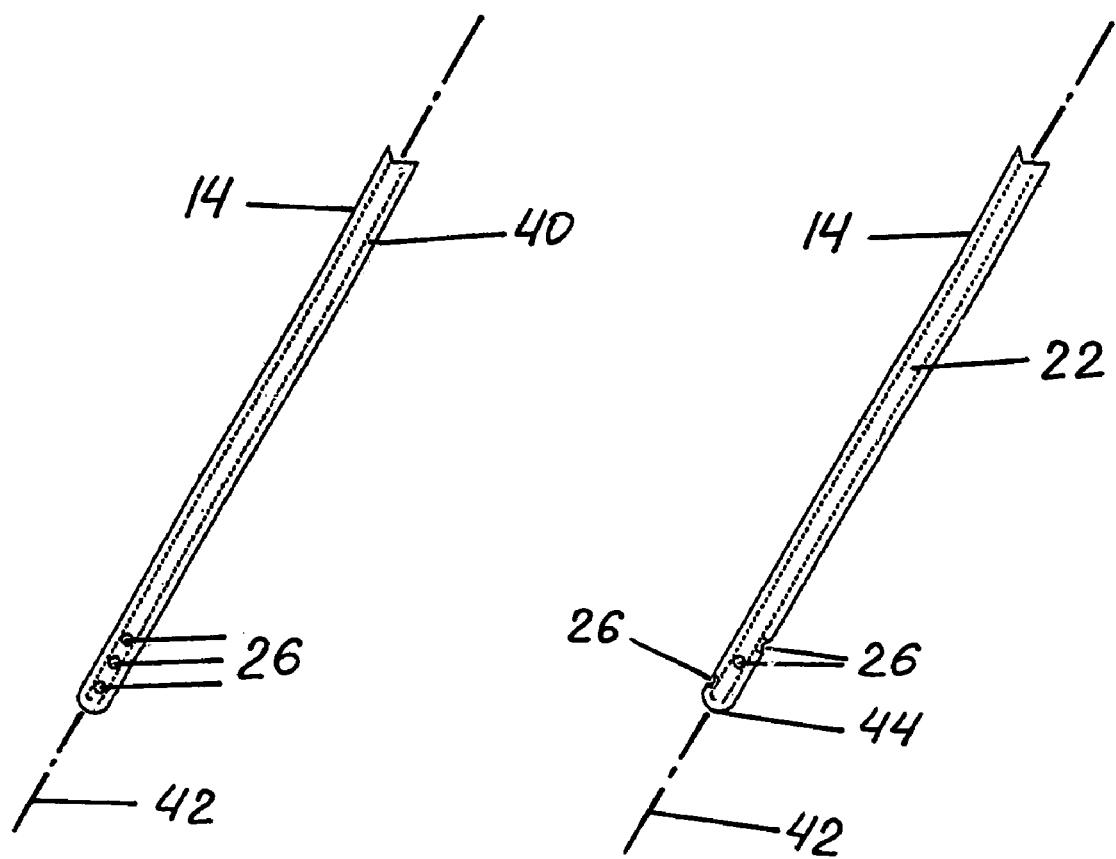
FIGS. 4A and 4B are perspective views of the distal portions of alternate preferred inner catheters in accordance with this invention with dashed lines to represent otherwise unseen internal features.

The distal portion 40 of alternately preferred embodiments of inner catheter 14 are illustrated in FIGS. 4A and 4B. Each has a plurality of ports 26 in fluid communication with passageway 22. One arrangement of ports is depicted in FIG. 4A where each port 26 is spaced along distal portion 40 in axial alignment with central axis 42 of inner catheter 14. Another arrangement is seen in FIG. 4B where each port 26 is axially and radially spaced about distal portion 40. It should be understood that inner catheter 14 can have a port 26 coaxial with passageway 22 such as to form an open distal end 44 (as seen in FIG. 1) as well as or in addition to ports 26 positioned along the distal portion 40 adjacent to the distal end 44.

As seen in FIGS. 5A and 5B, preferred embodiments of outer catheter 12 can have a closed distal end 28 and a plurality of apertures 20. Apertures 20 in FIG. 5A are positioned above distal end 28 and spaced along exterior 46 of outer catheter 12 in axial alignment with central axis 48. Apertures 20 in FIG. 5B are shown axially and radially spaced about axis 48. One skilled in the art will recognize that these configurations may also include an aperture 20 forming an open distal end 28 as depicted in FIG. 1.

Each outer catheter 12 in FIGS. 5A and 5B also includes a distal portion 52 having a reduced diameter. Such a configuration for distal portion 52 allows for reduced injury to the surrounding tissue regions during the insertion of outer catheter 12 into the brain.

Outer catheter 12 also preferably includes elements 50 secured to distal portion 52. Elements 50 provide for monitoring of brain activity, for stimulating brain tissue or for serving as a location beacon to aid in determining the precise position of the distal portion 52 within the brain. Elements 50 communicate with external monitoring and control equipment during treatment of the patient. Such communication can be by way of electrical, optical and/or radio-frequency transmission.

Elements 50 can take the form of contacts 54, as illustrated in FIGS. 1, 3 and 5. Contacts 54 comprise devices such as electrodes 55 designed to monitor brain activity in tissue region 38 through the sensing of electrical and/or electrochemical changes within the brain as well as electrodes 56 designed to provide electrical stimulation to specific areas of the brain. Electrodes serving as contacts 54 are preferably constructed from platinum, platinum-iridium or other biocompatible conductive material. Electrodes can be macrocontacts that circumscribe or band outer catheter 12 or microcontacts 57 capable of measuring electrical changes at the level of a single neuron.

Elements 50 can also can take the form of a sensor 58 as depicted in FIG. 3. Sensors 58 are designed to monitor brain activity within select tissue regions through the sensing of electrical, electrochemical, chemical, temperature or pressure changes within the brain. Sensors 58 can be electrochemical and optical transducers designed to measure chemical, pressure, temperature, cerebral blood flow and other physiological changes in the brain. Such devices are known in the art and are preferably less than about 2 millimeters long. Sensor 58 is preferably in the form of a chemical sensor.

Contacts 54 and sensors 58 of outer catheter 12 are preferably connected by leads 60 (seen in FIG. 6A running alongside lumen 16) to proximal-contacts 62. Leads 60 can be in the form of electrical wiring or a fiber-optic bundle. Proximal-contacts 62 are mounted along the outer catheter's proximal portion 64 as shown in FIGS. 1, 3, 5 and 6. Brain activity sensed by contacts 54 and sensors 58 is transmitted to a computer or similar instrument having a conventional output display and monitor with a suitable power source via an external connector in operative communication with proximal-contacts 62 where such activity can be recorded and/or analyzed. During insertion of such embodiments of outer catheter 12 into the brain, proximal-contacts 62 remain outside of the patient. Proximal-contacts 62 are preferably formed from stainless steel or similar alloys or materials that are non-corrosive conductors and that can endure sterilization.

Figure 7:
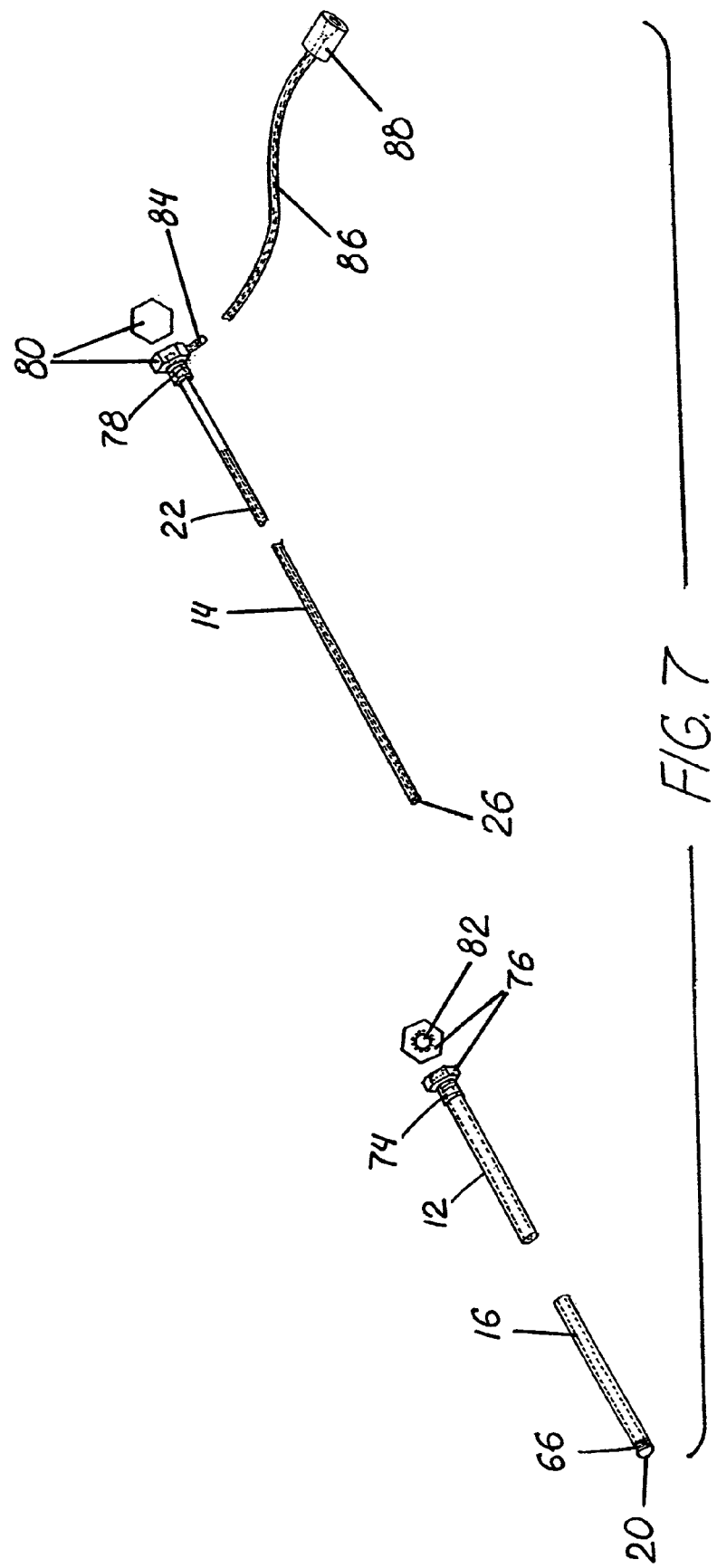
FIG. 7 is a perspective view of another preferred outer catheter and inner catheter in accordance with this invention with cut-away sections and dashed lines representing otherwise unseen internal features along with top views of the heads of both catheters.

Element 50 can also take the form of a location marker 66 as seen in FIGS. 1 and 7. Location marker 66 is preferably a structure comprised of a non-ferrous material known in the art such as gold or tungsten that has an image signal intensity suitable for proton magnetic resonance imaging (MRI) with most commercial machines and is also sufficiently x-ray opaque for satisfactory imaging using computed tomographic scanning (CT) or on X-ray. Location marker 66 can also be comprised of a sensor capable of measuring voltages induced by a transmitted magnetic field that can be used to identify the position and orientation of the sensor within that field.

Elements 50 may be positioned on both the distal and proximal sides of apertures 20 along distal portion 52 as seen in FIGS. 5A and 5B. This configuration allows for monitoring of cellular function within the tissue region of the brain 38 prior to treatment to verify the presence of diseased brain cells. Upon verification of diseased tissue within the targeted region, delivery of a drug or other treatment agent can commence through inner catheter 14 while monitoring of the tissue region 38 continues concurrently with such treatment. This can have particular value in the treatment of different tissue regions of the brain for movement disorders such as Parkinson's Disease.

Micro-contacts 57 can be spaced axially along distal portion 52 as illustrated in FIG. 5B or spaced radially around outer catheter 12 as shown in FIG. 5A.

FIGS. 6A and 6B illustrate an outer catheter 12 having an inflatable balloon 68 rigidly mounted to exterior 46, preferably above at least one element 50. As seen in FIG. 6A, a conduit 70 enters outer catheter 12 along proximal portion 64 and runs alongside lumen 16, terminating at balloon 68. Conduit 70 is preferably tubing made of polyurethane. Conduit 70 provides for the introduction of a fluid to inflate balloon 68 and, if necessary to withdraw fluid from balloon 68 to cause deflation. Conduit 70 originates at injection port 72 that can be operatively connected to an external device such as a pump to dispense or receive fluid.

Following placement of outer catheter within the brain, balloon 68 can be inflated to block or occlude the insertion tract 69 created during the insertion process so that any drug administered to the brain through aperture 20 cannot migrate back through that tract. Balloon 68 is preferably made from an elastomeric material to achieve complete deflation of balloon 68 when outer catheter 12 is later withdrawn from the brain.

In certain embodiments, balloon 68 is permeable. Balloon 68 in these embodiments can be inflated with a drug or other fluid intended to be administered to the brain whereby the drug then permeates through the wall of balloon 68 to treat the tissue region 38 surrounding balloon 68. In this manner, a drug can be introduced to one targeted tissue region of the brain delivered by inner catheter 14 through aperture 20 at the same time the same or a different drug is transferred to another selected tissue region through permeable balloon 68. Balloon 68 is preferably adapted to administering a drug to the brain slowly over a period of time, thereby allowing for the effective introduction of the drug to the desired tissue region 38. This is especially desirable where there is a void in the particular tissue region due to some structure such as a tumor being removed. Inflating balloon 68 within the void permits the medication to be more effectively transferred to all of the affected tissue that surrounds the outside of the balloon.

One skilled in the art will recognize that balloon 68 can be made permeable by forming balloon 68 from a naturally porous material such as polytetrafluroethylene (PTFE) or from an elastomeric material having perforations formed in the wall of the balloon. The balloon wall is preferably from 0.5 to 5.0 mils in thickness. Where the balloon wall is perforated, an array of minute perforations, each having a diameter of 5 to 30 microns, is preferably uniformly spaced apart and concentrated along a central band circumscribing balloon 68. Concentration of the perforations within such a region in the middle of balloon 68 provides for focused delivery of the drug by limiting the area of permeation to just the surface area of balloon 68 making conforming contact with the surrounding brain tissue.

Figure 8:
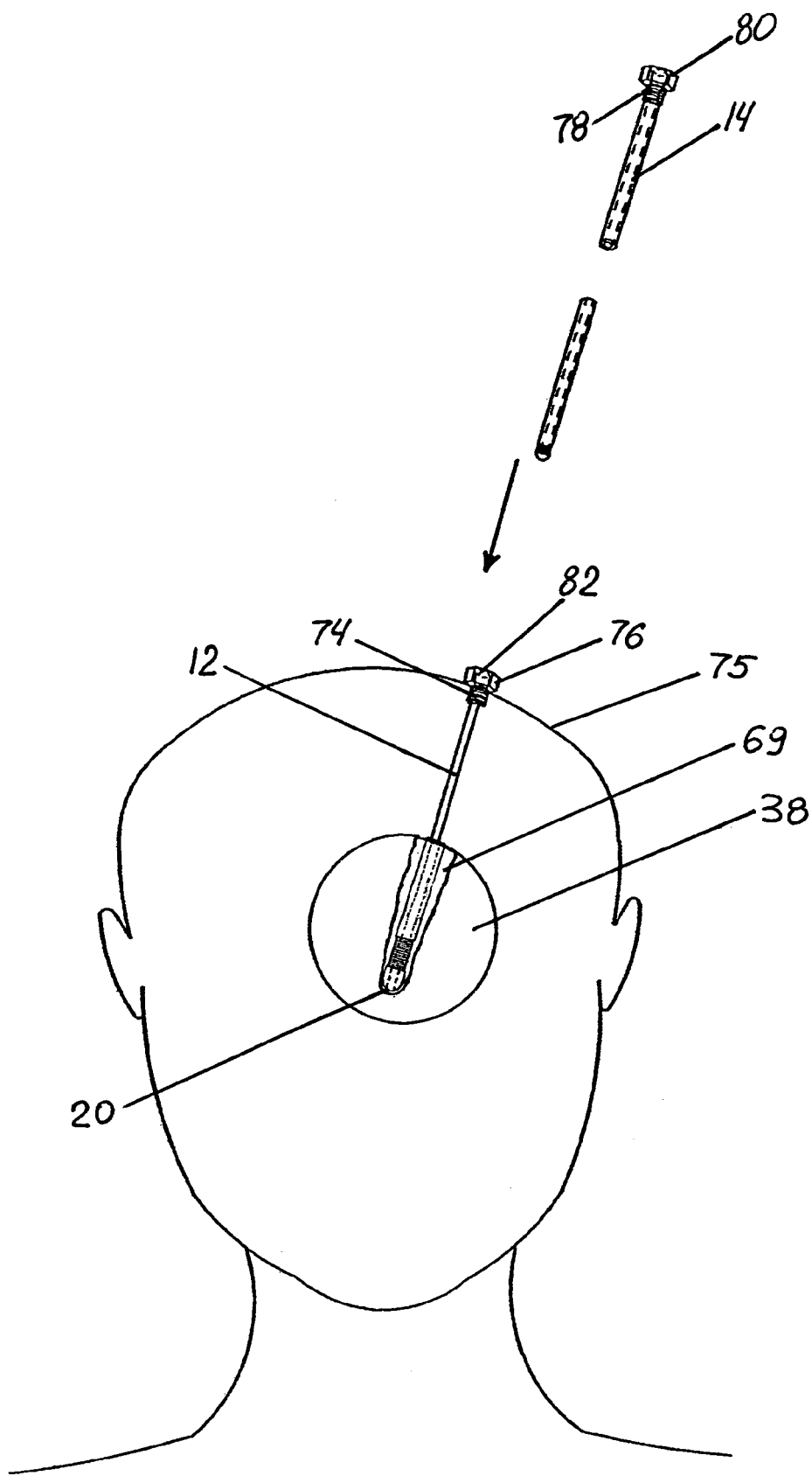
FIG. 8 is a schematic view illustrating the outer catheter of FIG. 7 positioned within the brain and prepared to receive the inner catheter of FIG. 7.

As shown in FIGS. 7 and 8, outer catheter 12 can further include a threaded exterior portion 74. Threaded portion 74 preferably abuts a hexagonal head 76 at the proximal end 30 of outer catheter 12. Outer catheter 12 can be firmly secured to the patient by screwing threaded portion 74 into the skull 75 using the head 76 of the catheter.

Each inner catheter 14 comprising catheter system 10 with this embodiment of outer catheter 12 also includes a threaded proximal portion 78 immediately beneath the head 80 of inner catheter 14. Head 76 of outer catheter 12 is provided with a threaded opening 82 coaxial with lumen 16. Upon inserting inner catheter 14 through opening 82 into lumen 16, inner catheter 14 is firmly secured to outer catheter 12 by screwing threaded portion 78 into threaded opening 82 utilizing head 80.

Outer catheter 12 in this manner serves as a trajectory catheter. Outer catheter 12 preferably includes location marker 66 to aid in positioning outer catheter 12 at the desired location in a targeted tissue region of the brain 38. Head 80 of inner catheter 14 is preferably provided with a fitting 84 in communication with passageway 22 to which a flexible conduit 86 such as polyurethane tubing can be attached. Conduit 86 extends outward and terminates at a tapered inlet 88. Tapered inlet 88 is preferably a luer fitting to which an external apparatus such as a pump can be connected to permit a liquid treatment agent or other fluid to be injected into and/or withdrawn from tissue region 38.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A catheter system for intracranial treatment of a patient comprising:
   an outer catheter having an opening, at least one open aperture at a distal end, and a lumen in communication with respect to the opening and the aperture, the aperture being coaxial with the lumen and the outer catheter being adapted for insertion into the brain of the patient; and
   at least first and second inner catheters chosen from a plurality of different inner catheters for delivering a treatment agent to a select tissue region of the patient's brain, each inner catheter having a substantially identical outer diameter so that each inner catheter is adapted to be individually received within the lumen, the lumen snugly receiving each inner catheter and guiding each inner catheter to the tissue region, each inner catheter being adapted to extend through the aperture when inserted into the lumen and having a passageway and at least one port in communication with the passageway, the first inner catheter having a first length for delivering the treatment agent to a first tissue region and the second inner catheter having a second length for delivering the treatment agent to a second tissue region.

2. The catheter system of claim 1 wherein the second length is greater than the first length such tat the second tissue region is at a greater distance distal from the aperture than the first tissue region.

3. The catheter system of claim 1 wherein each inner catheter has a distal end and the port on each inner catheter is positioned at the distal end.

4. The catheter system of claim 1 wherein each inner catheter has a different arrangement of a plurality of ports.

5. The catheter system of claim 1 wherein the treatment agent is a fluid.

6. The catheter system of claim 5 wherein the fluid is a drug.

7. The catheter system of claim 5 wherein the passageway of the first inner catheter has a first diameter and the passageway of the second inner catheter has a second diameter, the second diameter being greater than the first diameter such that the delivery of the fluid to the second tissue region is at a different flow rate than the delivery of the fluid to the first tissue region.

8. The catheter system of claim 1 wherein the at least one aperture is a first aperture, the outer catheter further includes a second aperture, and the outer catheter has an axis and an exterior, the second aperture being spaced apart axially from the first aperture along the exterior.

9. The catheter system of claim 8 wherein the outer catheter further includes a third aperture, the second and third apertures being spaced radially about the axis along the exterior.

10. The catheter system of claim 1 wherein the outer catheter includes an element adapted to monitor brain activity within the tissue region, to electronically stimulate the tissue region, or to provide information on a precise position of the element when the element is located entirely within the brain.

11. The catheter system of claim 10 wherein the brain activity being monitored is electrical activity.

12. The catheter system of claim 10 wherein the element is a micro-contact.

13. The catheter system of claim 10 wherein the element is a sensor.

14. The catheter system of claim 13 wherein the sensor senses chemical activity.

15. The catheter system of claim 10 wherein the element is a location marker to identify the position of the outer catheter within the brain.

16. The catheter system of claim 10 wherein the element is mounted proximal to a distal end of the outer catheter upon an exterior surface of a distal portion of the outer catheter.

17. The catheter system of claim 1 wherein the outer catheter further includes a proximal portion, an exterior, and a conduit extending from the proximal portion to an inflatable balloon secured to the exterior.

18. The catheter system of claim 17 wherein the balloon is inflatable with at least one drug and the balloon is formed from a material permeable to the drug such that the drug can be introduced into the brain through the balloon.

19. The catheter system of claim 17 wherein the balloon is positioned along the outer catheter proximally adjacent to the aperture, the balloon being adapted to seal upon inflation a tract created upon insertion of the outer catheter into the brain.

20. The catheter system of claim 17 wherein the balloon is positioned along the outer catheter proximal to at least one element.

21. The catheter system of claim 1 wherein the outer catheter has a proximal end and the opening is positioned at the proximal end.

22. The catheter system of claim 21 wherein the outer catheter has a tapered fitting at the proximal end, the tapered fitting being configured for removable engagement to a fitting at a proximal end of each inner catheter.

23. The catheter system of claim 22 wherein the tapered fitting on the outer catheter is snugly received within the fitting on each inner catheter.

24. The catheter system of claim 21 wherein the proximal end abuts a threaded exterior portion such that the outer catheter may be screwed into the skull of the patient after the outer catheter is placed in a targeted area within the patient's brain.

25. The catheter system of claim 24 wherein the first inner catheter is threadably received by the outer catheter to firmly secure the inner catheter to the outer catheter.

26. The catheter system of claim 1 wherein the outer catheter has a diameter between about 0.6 millimeters and 3.0 millimeters.

27. The catheter system of claim 26 wherein the diameter is about 1.0 millimeters.

* * * * *

UNITED STATES PATENT AND TRADEMARK OFFICE
CERTIFICATE OF CORRECTION

PATENT NO. : 7,465,292 B2
APPLICATION NO. : 11/262376
DATED : December 16, 2008
INVENTOR(S) : David A. Putz Page 1 of 1

It is certified that error appears in the above-identified patent and that said Letters Patent is hereby corrected as shown below:

Column 5, line 36, after "includes", delete "baying" and insert --having--.

Column 11, line 29, after "such", delete "tat" and insert --that--.

Signed and Sealed this

Seventeenth Day of March, 2009

JOHN DOLL
*Acting Director of the United States Patent and Trademark Office*